US010368154B2

(12) United States Patent
Blau et al.

(10) Patent No.: US 10,368,154 B2
(45) Date of Patent: Jul. 30, 2019

(54) SYSTEMS, DEVICES AND METHODS FOR EXECUTING A DIGITAL AUDIOGRAM

(71) Applicant: Listening Applications LTD., Jerusalem (IL)

(72) Inventors: Yoav Blau, Tel Aviv (IL); Tomer Shor, Jerusalem (IL); Yehonatan Roth, Jerusalem (IL); Sabrina Cohen, Jerusalem (IL)

(73) Assignee: Listening Applications Ltd., Jerusalem (IL)

( * ) Notice: Subject to any disclaimer, the term of this patent is extended or adjusted under 35 U.S.C. 154(b) by 0 days.

(21) Appl. No.: 16/053,536

(22) Filed: Aug. 2, 2018

(65) Prior Publication Data

US 2019/0045293 A1 Feb. 7, 2019

Related U.S. Application Data

(60) Provisional application No. 62/655,845, filed on Apr. 11, 2018, provisional application No. 62/540,074, filed on Aug. 2, 2017.

(51) Int. Cl.
*H04R 1/10* (2006.01)
*H04R 29/00* (2006.01)
(Continued)

(52) U.S. Cl.
CPC ......... *H04R 1/1041* (2013.01); *A61B 5/0004* (2013.01); *A61B 5/0022* (2013.01);
(Continued)

(58) Field of Classification Search
CPC ...... H04R 1/1041; H04R 3/04; H04R 29/001; H04R 2420/07; G10K 11/17823;
(Continued)

(56) References Cited

U.S. PATENT DOCUMENTS 4,284,847 A 8/1981 Besserman
6,840,908 B2 1/2005 Edwards et al.
(Continued)

FOREIGN PATENT DOCUMENTS

WO 2006002036 A2 1/2006

OTHER PUBLICATIONS

Abram Bailey and Brian Taylor, "Smartphone Applications for Private Practice Audiologists", Academy of Doctors of Audiology, (Power Point Presentation).

*Primary Examiner* — Mark Fischer
(74) *Attorney, Agent, or Firm* — Mark David Torche; Patwrite Law

(57) ABSTRACT

A system for providing audio output. The system includes a device, e.g. a mobile phone connectable to one or more earphones. The device includes a computing platform having a processor; an audio unit configured to generate one or more output signals of arbitrary amplitude to the earphone(s); and at least one microphone configured to record the ambient power level during signal output. The user indicates his/her hearing of the output signals whereby a proportionality constant is recorded for each frequency of the output signals. The processor is configured to: analyze the proportionality constant for each frequency of one or more feedback signals from the earphone(s) to yield calibration data; adjust the amplitude or frequency based on the calibration data; generate one or more audiograms resulting from a hearing test; and adjust the device power level according to the received one or more audiograms.

17 Claims, 12 Drawing Sheets

(51) Int. Cl.
*H04R 3/04* (2006.01)
*G10K 11/178* (2006.01)
*A61B 5/12* (2006.01)
*A61B 5/00* (2006.01)

(52) U.S. Cl.
CPC ............ *A61B 5/125* (2013.01); *A61B 5/6803* (2013.01); *A61B 5/7203* (2013.01); *A61B 5/725* (2013.01); *G10K 11/17823* (2018.01); *G10K 11/17853* (2018.01); *H04R 3/04* (2013.01); *H04R 29/001* (2013.01); *G10K 2210/1081* (2013.01); *G10K 2210/3028* (2013.01); *H04R 2420/07* (2013.01)

(58) Field of Classification Search
CPC ..... G10K 11/17853; G10K 2210/1081; G10K 2210/3028; A61B 5/0004; A61B 5/0022; A61B 5/125; A61B 5/6803; A61B 5/7203; A61B 5/725
See application file for complete search history.

(56) References Cited

U.S. PATENT DOCUMENTS

| | | | |
|---|---|---|---|
| 7,149,684 | B1 | 12/2006 | Ahroon |
| 7,210,353 | B2 | 5/2007 | Braun et al. |
| 7,736,321 | B2 | 6/2010 | Wasden et al. |
| 8,529,464 | B2 | 9/2013 | Wasden et al. |
| 9,031,247 | B2 | 5/2015 | Shennib |
| 9,326,706 | B2 | 5/2016 | Shennib |
| 9,532,152 | B2 | 12/2016 | Shennib |
| 9,807,526 | B2 | 10/2017 | Choi et al. |
| 9,894,450 | B2 | 2/2018 | Shennib |
| 2003/0083591 | A1* | 5/2003 | Edwards ............... A61B 5/121 600/559 |
| 2011/0200217 | A1* | 8/2011 | Gurin .................... A61B 5/123 381/320 |
| 2014/0166122 | A1* | 6/2014 | Goldstein ........... H04R 1/1041 137/223 |
| 2015/0358745 | A1 | 12/2015 | Rix et al. |
| 2017/0053639 | A1* | 2/2017 | Lu ........................ G10K 11/178 |
| 2017/0300292 | A1* | 10/2017 | Torrini .................. A61B 5/125 |

\* cited by examiner

SYSTEMS, DEVICES AND METHODS FOR EXECUTING A DIGITAL AUDIOGRAM

CROSS-REFERENCE TO RELATED APPLICATIONS

The present application claims the benefit of U.S. Provisional Application Ser. No. 62/540,074 filed on 2 Aug. 2017, entitled "SYSTEM AND METHOD FOR REMOTE AUDIOLOGY TESTING", which is incorporated herein by reference in its entirety. The present application also claims the benefit of U.S. Provisional Application Ser. No. 62/655,845 filed on 11 Apr. 2018, entitled "SYSTEMS, DEVICES AND METHODS FOR EXECUTING A DIGITAL AUDIOGRAM", which is incorporated herein by reference in its entirety.

FIELD OF THE INVENTION

The present invention relates in general to audiology, more particularly to audiometric testing and usages thereof.

BACKGROUND OF THE INVENTION

Hearing tests are generally conducted by hearing institutes or laboratories, and are performed using specialized medical devices such as audiometers, special headphones and sealed rooms. The most common type of audiometer generates pure tones, with varying amplitudes as chosen by a human operator, typically a hearing specialist, and delivered to the subject's ears through the headphones. During testing, the subject indicates that a tone was heard by pressing a feedback button or by a visual signal to the operator. The audiometer enables the operator to produce an audiogram, describing the subject's hearing acuity.

Current methods and systems for performing the hearing tests can be less than ideal in at least some respects. Presently, the art requires expensive equipment and an audio specialist using specialized medical devices, as part of the hearing test to get accurate results. This requires substantial expense and time, thereby preventing many end users from receiving adequate hearing testing, or hearing surveillance, which could help to identify and prevent hearing deterioration. A practical method for tracking such deterioration was suggested by the Occupational Health Service for the Northern Ireland Civil Service (MacLurg et al., 2004). The analysis they provide may serve as guidelines to produce alerts or advice regarding the state of a user's hearing. However, this requires that the user undergoes periodic hearing tests.

SUMMARY OF THE INVENTION

There are provided, in accordance with embodiments, an improved audiology testing system, device and method, which may be performed using standard devices such as a laptop, tablet computer, media console, personal digital assistant or smart phone, or any other sort of device having a processor and audio unit for example a user's mobile phone, for performing a clinical hearing test (i.e. remote audiology testing).

In some embodiments, the clinical hearing test is performed without expert intervention and without a medical device.

In some embodiments, the audiology testing system includes components for facilitating remote audiology for example, a mobile device, headphones; and a microphone such as a sound level meter (SLM).

In some embodiments, a system is provided for providing audio output. The system includes: a device connectable to an earphone, the device including a computing platform having a processor; an audio unit configured to generate one or more output signals of arbitrary amplitude to the earphone; a microphone configured to record the power level of said outputs signals and calculate a proportionality constant for each frequency of said output signals; and wherein the processor is further configured to: analyze the proportionality constant for each frequency of one or more feedback signals from said earphone to yield calibration data; adjust the amplitude or frequency based at least on the calibration data to calibrate the device; generate one or more audiograms resulted by conducting a hearing test using the calibrated device; adjust said device power level according to said received one or more audiograms.

In some embodiments the processer is configured to calculate a fractional amplitude coefficient for each of said feedback signals for providing said calibration data.

In some embodiments the hearing test is executed by said processor according to a state deterministic automaton.

In some embodiments the hearing test is based on the Hughson-Westlake technique.

In some embodiments the audiograms are applied to one or more selected remote devices having a processor, said processor is configured to adjust the selected device audio power based on the audiograms.

In some embodiments the device is a mobile communication device including wireless communication circuitry to communicate with a remote server, and wherein the processor including instructions to transmit the audiogram to the remote server.

In some embodiments, in response to the instructions the audiograms are further integrated in the remote server database for adjusting an audio output control of one or more contents or application in the remote server database in accordance with the integrated audiogram.

In some embodiments the audiograms are applied to a communication layer of communications provider of the remote server for adjusting an audio output control of the communication layer of communications provider in the remote server database in accordance with the integrated audiogram.

In some embodiments the content or application is selected from the group consisting of: YouTube, iTunes, Google Play Music, Netflix, audiobooks, radio stations, conferencing software.

In some embodiments the earphone is selected from a group consisting of: noise cancellation earphones, wireless earphones, wired earphones.

In some embodiments the microphone is a sound level meter (SLM).

In some embodiments the audiograms are stored, distributed, or shared in a digital format.

In some embodiments the audiograms include personal preferences of said user.

In some embodiments the audiograms are shared with other devices, cloud services, or applications.

In some embodiments the other devices or applications are selected from the group consisting of: computers, PCs, mobile devices, televisions, YouTube, Netflix, cable TV, Spotify, Apple music, Google Play Music, online radio stations, games.

In some embodiments the audiograms are shared with other devices via a network server.

In some embodiments the audiograms are applied to a cloud-based Conference Call program, to improve output to conference call users.

In some embodiments the audiograms are applied to digital assistant devices.

In some embodiments the digital assistant devices are managed by user interfaces, optionally Artificial Intelligence (AI) driven interfaces, for example Amazon's Alexa, Microsoft's Cortana, Apple's Siri, Samsung's Bixby, or other AI assistants.

In some embodiments the audiograms are applied to broadcast radio.

In some embodiments the audiograms are applied to an audio output channel to provide audio output adapted to a user's accent or dialect.

In some embodiments the audiograms are integrated into a processor of noise cancellation earphones for converting said noise cancellation earphones to audio enhancing devices or hearing aid devices.

In some embodiments the conversion includes filtering audio signals received at the noise cancellation earphones and amplifying audio signals yield a personalized audio output by the noise cancellation earphones.

According to some embodiments, a method is provided for providing audio output using a device including an audio unit and a processor, and wherein the device is further connectable to an earphone, the method including: performing a hearing test to a user using the device, the hearing test including generating signals at selected frequencies and hearing levels and recording the user feedback; generating a digital audiogram profile based on the hearing test; transmitting said digital audiogram to the device or to a remote server; and converting the digital audiogram to an audio filter; adjusting the device audio output to yield an audio output.

In some embodiments, the method includes converting the digital audiogram to an audio filter includes shaping input signal so as to be amplified by a magnitude equivalent to the audiogram's gain level for each tested frequency, or some other frequency response derived from said digital audiogram, for example 50% the gain levels.

In some embodiments, the method includes adjusting the device audio output is configured by applying the audio filter, or other filters which may be beneficial for the user, such as noise reduction, or band-pass filtering.

According to some embodiments, a server-based audiogram analysis engine system is provided, the system including: a remote server, the remote server is in communication with a database and a remote processor; a plurality of remote devices connectable respectively to a plurality of earphones, wherein each of the plurality of remote devices includes: a computing platform having a processor; an audio unit configured to generate respectively one or more output signals of arbitrary amplitude to said plurality of headphones; wireless communication circuitry to communicate with the remote server; and wherein each of the remote devices is configured to: perform a hearing test to one or more users, the hearing test includes: generating one or more output signals of arbitrary amplitude to yield an audiogram profile respectively for each of the users; transmit the audiogram profile to said remote server, wherein the remote server includes instructions to: analyze the audiogram profiles; convert the audiogram profiles to yield a personalized audio filter for each of a plurality of remote devices.

In some embodiments the analysis includes generating one or more alerts.

According to some embodiments, noise-canceling headphones are provided that is connectable to a portable computing platform having a processor, the noise-canceling headphones including: an electro-acoustic transducer converting ambient noise into a noise signal; a cancel signal generator generating and outputting a cancel signal to eliminate the noise from the noise signal; and a speaker unit outputting an audio signal and the cancel signal, wherein the processor is configured to: receive one or more audiograms; convert the audiograms as a function of the frequency in which a hearing gain level was established for the user; filter the cancel signal based on said function to transform the noise-canceling headphones into a hearing aid.

In some embodiments the audiogram is a digital audiogram.

In some embodiments the digital audiogram is obtained by performing a hearing test using the above described system.

A machine-readable non-transitory medium is herein provided, encoded with executable instructions for transforming the noise-canceling headphones into a hearing aid, the instructions including code for: converting one or more audiograms of a user of the noise-canceling headphones as a function of the frequency in which a hearing gain level was established for the user; and filtering a cancel signal based on the function to transform said noise-canceling headphones into a hearing aid.

Potential advantages of some embodiments of the present invention include that it could enable conducting remote hearing tests using non-specialist equipment, with high accuracy, for example at home or out of a laboratory, thereby avoiding the inconvenience and/or the expense of going to doctors and/or clinics and using standard devices such as a personal computer (PC), tablet, smartphones, and earphones, for convenient, accessible, user-friendly, efficient and economical operation.

BRIEF DESCRIPTION OF THE DRAWINGS

The principles and operation of the system, apparatus, and method according to the present invention may be better understood with reference to the drawings, and the following description, it being understood that these drawings are given for illustrative purposes only and are not meant to be limiting, wherein.

DETAILED DESCRIPTION OF EMBODIMENTS OF THE INVENTION

Figure 1:
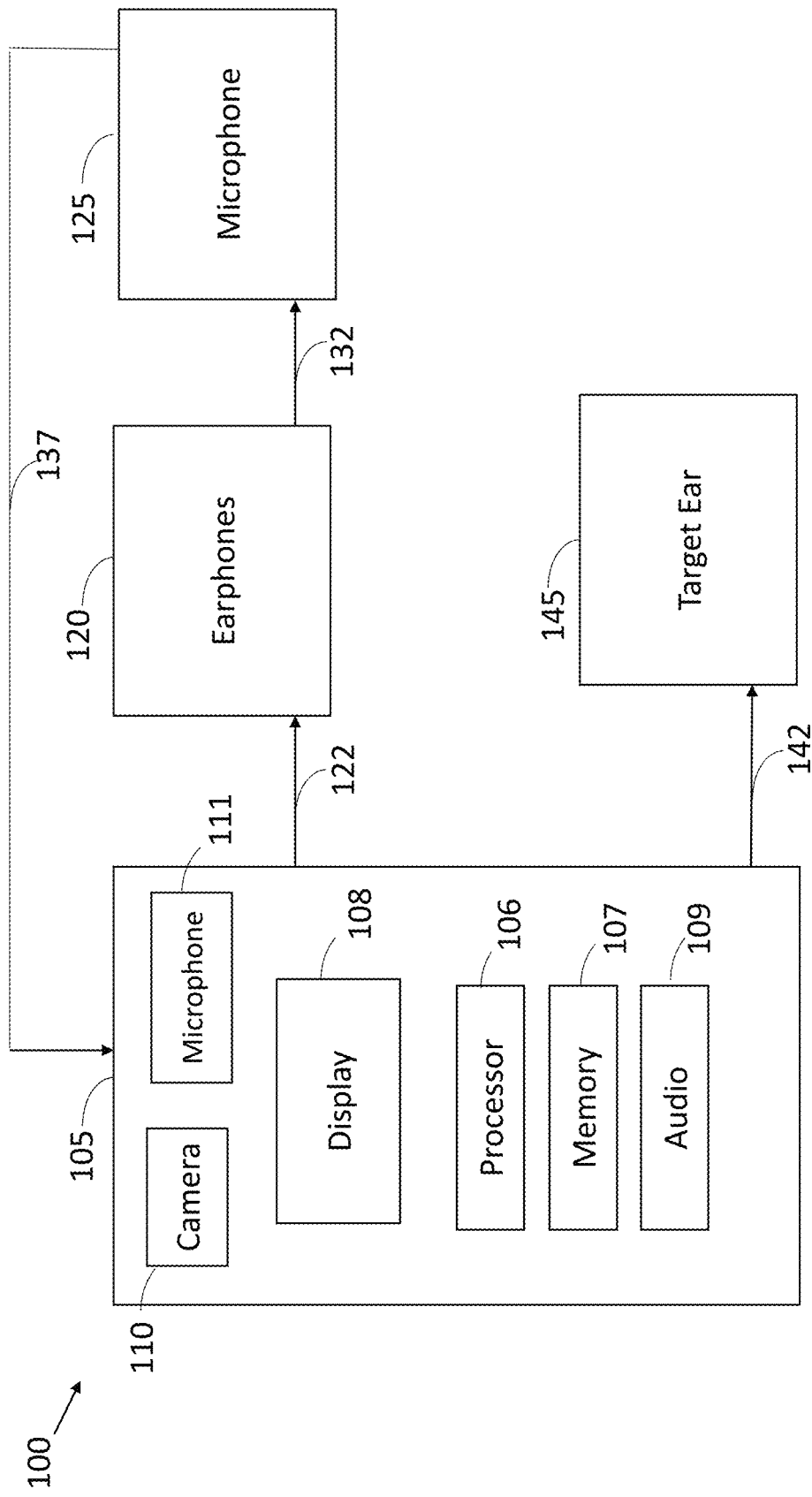
FIG. 1 is a schematic system diagram depicting an audiology system, in accordance with embodiments of the present invention.

The following description is presented to enable one of ordinary skill in the art to make and use the invention as provided in the context of a particular implementation and its requirements. Various modifications to the described embodiments will be apparent to those with skill in the art, and the general principles defined herein may be applied to other embodiments. Therefore, the present invention is not intended to be limited to the particular embodiments shown and described, but is to be accorded the widest scope consistent with the principles and features herein disclosed. In other instances, well-known methods, procedures, and components have not been described in detail so as not to obscure the present invention.

There is provided, in accordance with embodiments of the present invention, an apparatus, system, and method configured and operable to perform audiologist functionalities on a computing device such as remote computing device or mobile device, including devices such as smartphones, laptops or notepads, standard headphones, and the like.

Non-limiting embodiments of the present invention include systems, devices methods and/or means for facilitating clinical audiometric testing at home or out of a laboratory, thereby avoiding the inconvenience and/or the expense of going to doctors and/or clinics to achieve the same. The increased accessibility may increase the number of people being tested and remove barriers for many with intermediate hearing loss. In this way, many people who are in need of being tested would have the sufficient hardware to perform the hearing test themselves. Furthermore, there are provided embodiments to facilitate recurring periodic tests, thereby enabling tracking of their hearing level and detect deterioration in their hearing abilities as soon as possible.

The term "gain level" as used herein the specification and claims should be understood to encompass dB HL (as defined for example by ANSI (1996)) and "gain jumps" in dB (decibels).

The term "headphones" or "earphones" as used herein the specification and claims should be understood to encompass earphones such as a sound receiver, which may be placed in or over the ear or held over the ear by a band or headset.

The term "Sound Level Meter" (SLM) as used herein the specification and claims should be understood to encompass an acoustic measurement unit such as a hand-held device including a microphone. For a given configuration, of hardware and software (e.g., system volume setting, digital signal amplitude, etc.), an SLM may set the reference power level in standard SPL units, which is Sound Pressure Level. Specifically, the SLM may be a microphone configured to handle a broad spectrum well and may be calibrated to assign different weights to each frequency band. In some cases, the audio the SLM records is accumulated periodically to produce one data point, the sound level. In some embodiments, no calibration may be required.

In accordance with some embodiments, the SLM is used to calibrate a remote testing system (e.g. including the user's mobile device such as the user's smartphone and headphones), therefore providing a virtual hearing aid. For example, in some cases, the SLM may be pressed against the user's headphones and record the power omitted when a tone is played by the user's device (e.g. smart phone) in each frequency at some amplitude level. This way, for each frequency, a proportionality constant is measured and determined. In some cases, following calibration, a testing setup produces tones of definite gain level, in hearing level (HL) units, enabling a precise audio test.

According to some embodiments, a remote audiology testing method and system is provided including calibrating a user's system including a mobile device such as a mobile phone connectable to one or more earphones and using the calibrated system for performing a remote hearing test.

In some cases, the mobile device is connectable to a portable computing platform having a processor, an audio unit and a microphone.

In some cases, the microphone is an SLM configured to calibrate the user's system (e.g. mobile device).

In some cases, an SLM is not required, rather the approximate frequency response of the user's hardware may be used, based on a calibration transfer.

In some embodiments, a method for executing a "calibration transfer" includes calibrating (e.g. the proportionality constant, or gain, per frequency) for a new type of device, subtracting (e.g. in logarithmic scale) the frequency response of one device, and adding (e.g. in logarithmic scale) the frequency response of another device, such that the new device can be calibrated, without ever having tested or used for such a test, wherein the new device calibration is hereinafter referred to as a "calibration transfer", and wherein, if all devices of the same type are similar, then the calibrating for one such device provides a calibration for all similar devices.

FIG. 1 shows a schematic system diagram depicting components in an audiology system 100, in accordance with embodiments of the present invention. The audiology system 100 is configured to facilitate remote audiology calibration using standard typical computer devices for example a portable or remote device (e.g. mobile phone), headphones and microphones and may be further used or configured as a virtual hearing aid for conducting a precise audiometric test. A virtual hearing aid may be defined, in accordance with some embodiments, as usage of non-specialized devices and systems such as standard hearing hardware and/or software to compensate for hearing loss or complement hearing difficulties, for example, changing audio output in accordance with a listener's hearing profile.

In some cases, the remote audiology system 100 includes a computerized device 105 such as a portable computing platform, earphones or headphones 120 and a microphone 125.

The device 105 may include, for example, a desktop, laptop, or tablet computer; a media console, a personal digital assistant or smart phone, or any other sort of device having a processor and audio unit. In some cases, the device 105 is configured to be in communication with a network, video and audio interfaces and computing capabilities needed to interact with a server. By way of example, device

105 may be a mobile device having a processor 106, memory 107, video display 108 and audio unit 109 including an audio input and output configured to generate and receive one or more audio signals, along with a video camera 110 and microphone 111 for recording.

Figure 10:
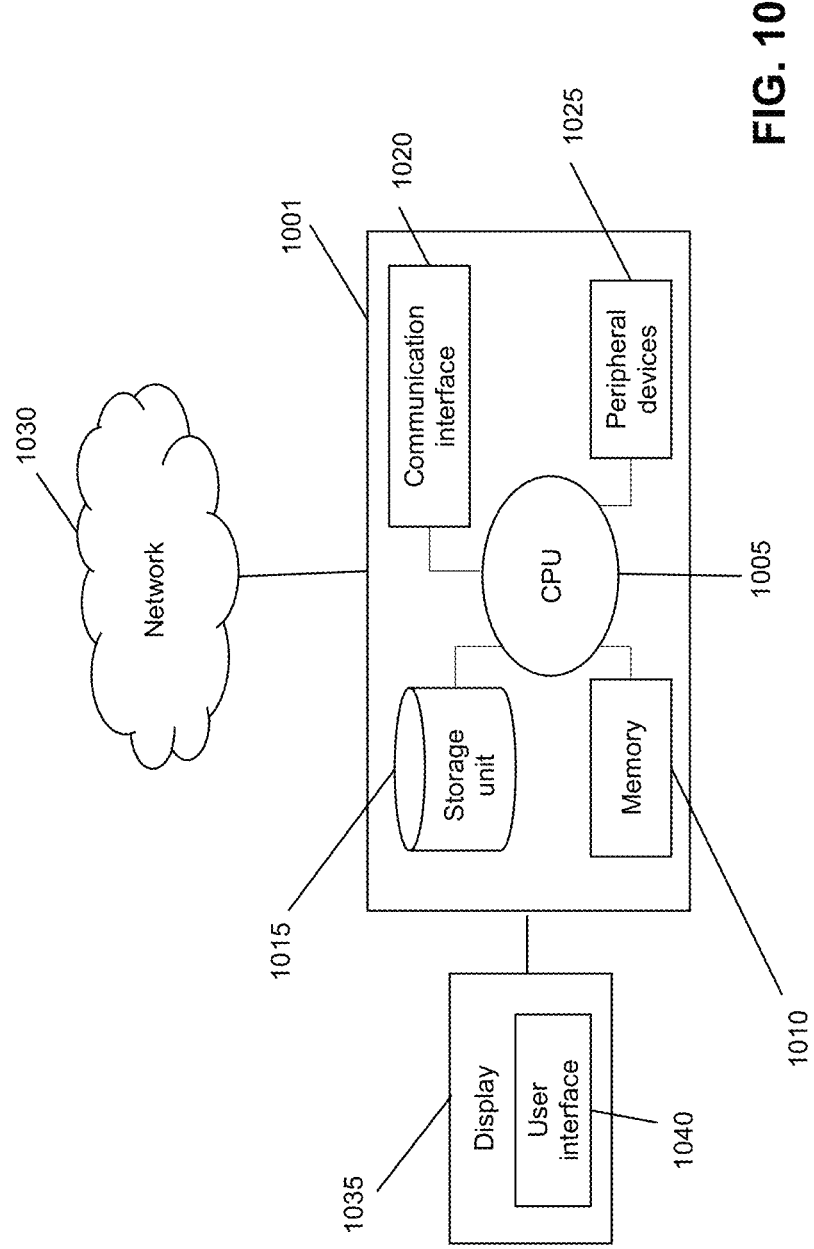
FIG. 10 shows a computer system suitable for incorporation with the methods and apparatus in accordance with some embodiments of the present invention.

In some cases, the device 105 is or includes units of a computer system 1001 illustrated in FIG. 10.

According to some embodiments, the headphones 120 are wired headphones, whereas in some embodiments the headphones are wireless headphones such as a Bluetooth™ headphones, for receiving audio input or tones 132 from device 105.

According to some embodiments, the microphone 125 is or includes a sound level meter (SLM).

In some cases the microphone 125 includes a measuring module for example in the form of software or firmware component configured to use an audio recorded by the microphone 125 to measure sound pressure level (SPL).

In operation, for a given configuration of hardware and software (e.g., system volume setting, fractional tone amplitude etc.), the microphone 125 (e.g. SLM) is configured to receive one or more tones 132 used to calibrate the audiology system 100 by setting a reference power level (for example in standard SPL units). The reference power level may be for example P0=20 µPa=0 dB SPL, as defined for example by IEC 60027-3:2002, and providing a coefficient magnitude 137, which is needed to amplify in each frequency to get the standardized hearing levels. Following the calibration process, the device 105 produces one or more tones 142 of definite gain level, for example in HL (hearing level) units towards a target ear 145, for conducting a precise audiometric test. The rightward-pointing arrows 122, 132 indicate the signal propagation, and the leftward-pointing arrow 137, going back from the microphone 125 to the device 105, indicates the measured values (feedback).

Figure 2:
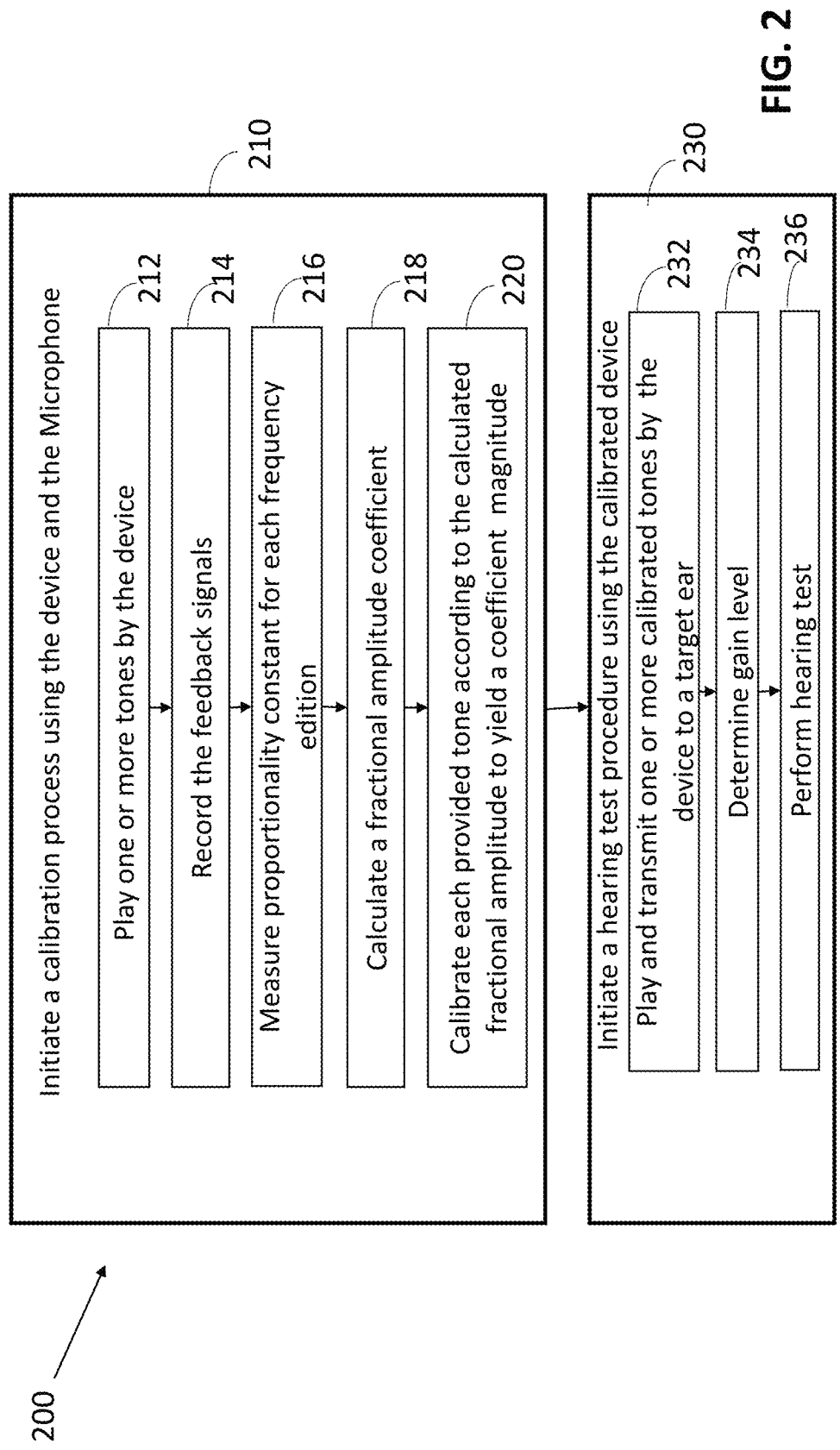
FIG. 2 is a flowchart of a method for performing an audiometric test, in accordance with embodiments of the present invention.

FIG. 2 is a flowchart 320 of a method 200 for performing an audiometric test, such as an audiometric self-test using a standard computerized system such as system 100, which includes a mobile device 105 (e.g. mobile phone) connectable to headphones 120 and a microphone 125, in accordance with embodiments. The standard computerized system is configured as a virtual hearing aid that may provide the mobile device user a hearing test anywhere he goes. At step 210 a calibration process is initiated, for example by a processor 106 of device 105 to set a reference sound power level (e.g. in standard SPL units). The calibration process may be operated for example using the microphone 125, and/or an SLM. In some cases, the calibration includes, at step 212, playing one or more tones by the device audio unit 109, for example near the headphones 120. The calibration may include transmitting from the device 105 to the headphones 120 one or more output signals such as pure tone signals, or signals including tones slightly modulated around a carrier frequency, or modulated by an envelope signal, of arbitrary amplitude (e.g. signals 122 of FIG. 1). The output signals may be "warbled" tones, which can take different shapes and may not be strictly speaking "pure" tones. In some cases, the tone is provided in each frequency at some amplitude level, for measuring for each frequency at some amplitude level. At step 214 the power emitted (e.g. feedback signals) by playing the tone in each frequency is recorded, for example at the device 105, and at step 216 the proportionality constant for each frequency is measured. In some cases, the measuring step is performed by recording feedback signals from the headphones membrane, treating it as a microphone or by the SLM. For example, the measuring step may be performed by creating an acoustic interface between the microphone 125, or SLM, and the headphones 120. Optionally, the signal is weighted properly (e.g. by A-weighting, as defined for example by international standard IEC 61672: 2003) and then its power is evaluated, which is linearly proportional to the signal's sound pressure level. At step 218 a fractional amplitude coefficient is calculated, for example by the device processor 106, and at step 220 each provided tone is calibrated according to the calculated fractional amplitude to yield a magnitude coefficient, which is needed to amplify the tone in each frequency to get the standardized hearing levels in dB HL, as defined for example by ANSI (1996).

Following the system's calibration procedure, the hearing testing procedure is initiated at step 230. Generally, the testing process includes producing tones of definite gain level, in HL (hearing level) units, enabling the system to conduct a precise audiometric test. Specifically, the hearing test includes at step 232 playing one or more calibrated tones transmitted from the device 105 to a target ear 145, for example via the headphones 120. At step 234 a gain level, which is required for providing an output tone, which includes the required power in hearing level (HL) standard scale, is determined to enable conducting a professional level hearing test. At step 236 a hearing test is performed.

Advantageously the system 100 and method 200 may be configured as a virtual hearing aid that provides the user with a hearing experience in multiple locations or environments where the user may be located. For example, the user may conduct a hearing test in his home or office, provided that the surrounding noise is lower than the user's threshold hearing, i.e. a quiet environment, as perceived by the user.

In some cases, the Virtual Hearing Aid (VHA) and the SLM are attached, by an acoustic interface, in a manner that continually delivers partial or full power emitted from the VHA via the headphones 120 to the SLM.

For example, system 100 may produce a specific gain $G_{out}^{dBHL}$ (in dBHL units) to be delivered to the subject ear, and the fractional amplitude of the produced sine wave would be:

$$A_{out}^{dB} = G_{out}^{dBHL} + T_{HL}(f) - P_{SLM}^{dBSPL}(f) + G_c$$

Where: f is the tone frequency, $P_{SLM}^{dBSPL}$ is the SLM power reading for a tone produced by the system 100 audio unit with fractional amplitude $G_c$, and $T_{HL}$ is a standard table converting dBSPL to dBHL units.

In some cases, an arbitrary global gain level $G_c$ is chosen, which permits recording emitted power by the microphone (e.g. SLM) for all or almost all target frequencies. With this gain level as fractional amplitude coefficient, the power is then recorded for tones in all target frequencies (for example 125, 250, 500, 750, 1000, 1500, 2000, 3000, 4000, 6000, 8000 Hz), for each ear. According to some embodiments, the tones are audio sample arrays of the shape $G_c \sin(2\pi f t)$.

In some cases, for a given frequency f a pure tone sine function with amplitude 1 is generated $\sin(2\pi f t)$. This tone may be amplified by a constant gain factor $G_{test}$. The signal is then multiplied by the test gain $H_{test}$ that achieves minimum audibility. The signal is multiplied by the system's volume factor V (matching the current state of the device 105) and is then produced by the soundcard/audio unit 109 $H_{sc}$ and transmitted to the headphones 120 $H_{hp}$.

In some cases, a subject threshold power (hearing level) in sound pressure level (SPL) $P_{th}^{SPL}$ can be expressed by:

$$P_{th}^{SPL}(\omega) = G_{test} H_{test-LR}(\omega) H_{sc}(\omega) H_{hp-LR}(\omega) L_{ear-LR}(\omega) \quad (1)$$

where $L_{ear0\text{-}LR}$ represents the subject's hearing loss as a function of excitation frequency.

Hearing impairment can be defined in this framework as having a threshold hearing higher than normal threshold hearing for some frequency. It is therefore assumed that the same values of $P_{th}$ are desired for all people, and hearing aids aim to set $$P_{th}(\omega) = P_{th}(\omega) L_{ear\text{-}LR}(\omega) H_{aid\text{-}LR}(\omega), \quad (2)$$

where the left-hand part of eq. (2) represents the threshold hearing of an ideally hearing human ear, and the right-hand part represents the threshold hearing of a person whose hearing is impaired by the loss function $L_{ear\text{-}LR}$ and corrected by a hearing aid supplying the gain function $H_{aid\text{-}LR}(\omega)$. The goal is to recover the latter and name this function the audiogram.

Using the calibration setup, one measures the output power from the sound level meter $P_{SLM}^{SP}(\omega)$ as a function of the source signal, amplified by $G_{calib}$ with test system volume set to V.

$$P_{SLM\text{-}LR}^{SPL}(\omega) = G_{calib} V H_{sc}(\omega) H_{hp\text{-}LR}(\omega) \quad (3)$$

Putting (3) into (1) one gets $$P_{th}^{SPL}(\omega) = G_{test} H_{test\text{-}LR}(\omega) G^{-1}{}_{calib} P_{SLM\text{-}LR}^{SPL}(\omega)$$
$$L_{ear\text{-}LR}(\omega). \quad (4)$$

One uses a conversion table $T_{HL}(\omega)$ to translate power in SPL to hearing level HL, such that $$P^{HL}(\omega) T_{HL}(\omega) = P^{SPL}(\omega) \quad (5)$$

This table has positive gain values, e.g. $T_{HL}$ (1 KHz)=7.5 dB.

One can now rewrite eq. (4) in HL and note that $P^{HL}{}_{th}$ is, by definition, unity.

$$P^{HL}{}_{th} = G_{test} H_{test\ LR}(\omega) G^{-1}{}_{calib} T^{-1}{}_{HL}(\omega) P^{SPL}{}_{SLM\text{-}LR}(\omega)$$
$$L_{ear\ LR}(\omega) \equiv 1 \quad (6)$$

Using eq. (2) one identifies the audiogram to be $$H^{HL}{}_{aid\text{-}LR}(\omega) = T^{-1}{}_{HL}(\omega) P^{SPL}{}_{SML\text{-}LR}(\omega)$$
$$G^{-1}{}_{calib} G_{test} H_{test\text{-}LR}(\omega) \quad (7)$$

Expressed in decibels, the audiogram ALR takes the form:

$$A_{LR} = -T_{HL}(\omega) + P^{SPL}{}_{SLM\text{-}LR}(\omega) - G_{calib} + G_{test} + H_{test\text{-}LR}(\omega) \quad (8)$$

To perform calibrated audio tests, and refrain from producing tones below 0 dBHL and above some maximum (for subject safety, and to keep within hardware dynamic range), it is required that the system produces tones of calibrated power. To produce a tone of specific gain (in dBHL) $K_{HL}$, the corresponding amplitude $K_{system}$ would be:

$$K_{system} = K_{HL\text{-}LR}(\omega) + G_{calib} - P^{SPL}{}_{SLM\text{-}LR}(\omega) + T_{HL}(\omega) \quad (9)$$

Where one used eq. (8), replacing the audiogram value $A_{LR}$ with the chosen tone level $K_{HL}$ and the corresponding test gain and gain factor $H_{test} + G_{test}$ with the output gain $K_{system}$. The calculated amplitude is in dB units. Its reference level depends on the hardware and volume settings. It is inconsequential as long as the setup remains unchanged.

It may be noted that, in accordance with some embodiments:

1. The system 100 (software, OS, soundcard, headphones) should remain the same throughout testing and calibration process. All volume controls are set to 50% for uniformity and a wide dynamic range;
2. It is assumed that the hearing test was conducted in a silent ambience and that calibration was performed far above any ambient noise, thus all noise factors are neglected; and
3. It is assumed that the (for example all) transmission functions are linear in power and do not change their behavior with respect to frequency. This is known to be approximately true for human hearing, and remains true for the system within its dynamic range. Otherwise, functions of frequency need to be replaced with functions of frequency and input power, and the calibration process becomes more involved.

In some embodiments, the method includes calibrating a system including for example standard devices, for example a virtual hearing aid based upon specialist usage of devices and systems such as device 105. The calibration is needed for controlling and/or adjusting the device's output signal power and to configure the device to perform clinical grade hearing tests.

In accordance with some embodiments, the calibration process includes: playing a digital audio signal (e.g. binary signal) including a list of integer amplitude values; a 16 bit pcm (or raw file), for example, has integer values from $-2^{15}$ to $2^{15}$; the soundcard converts this binary signal to an analog electric signal proportional to the amplitude values; the proportionality constant is different between different systems; the volume controls this constant.

Further, in some cases, for the calibration system or method, the microphone can be configured to perform the function of a Sound Level Meter (SLM), if it features a wideband frequency response. This is done by filtering the signal to assign different weights to different frequency bands (e.g. by A/B/C/D/Z-weighting, as defined by international standard IEC 61672:2003). The filtered audio is accumulated continuously or periodically, for example every second, to produce a measurement of the total received signal in units of SPL. The SLM may be used to calibrate the system, by pressing it against the headphones 120 and recording the power emitted when a tone is played in each frequency at some amplitude level. This way, for each frequency, the proportionality constant is known.

In this way, the SLM can be used to get the proportionality constant per frequency; for calculating how much to amplify the tone in each frequency to get the standardized hearing levels; and at this stage the calibrated tones can be played.

According to some embodiments, if all devices of the same type are similar, then calibrating for one calibrates for all, approximately. For example, sometimes the frequency response (the proportionality constant per frequency) may be known for a new type of device. In such a case, by subtracting the frequency response of one device and adding the frequency response of another, a new device can be calibrated, without ever having tested or used the new device. Calibration of the new device is hereinafter referred to as "a calibration transfer" or "a calibration projection."

In some embodiments, for example in mobile devices where the headphone's jack is also the mic jack, it may be possible to record feedback from the headphone's membrane, treating it as a microphone. Specifically, if a user places the headphones 120 on her/his ear and the system plays an impulse or tone, the impulse response may be recorded, for example immediately. Similarly, one could sweep through a wide range of frequency (slowly) and get the frequency response. In this way, the characteristics of unfamiliar devices may be acquired.

In accordance with some embodiments, one or more testing protocols may be used as part of the testing hearing.

Figure 3:
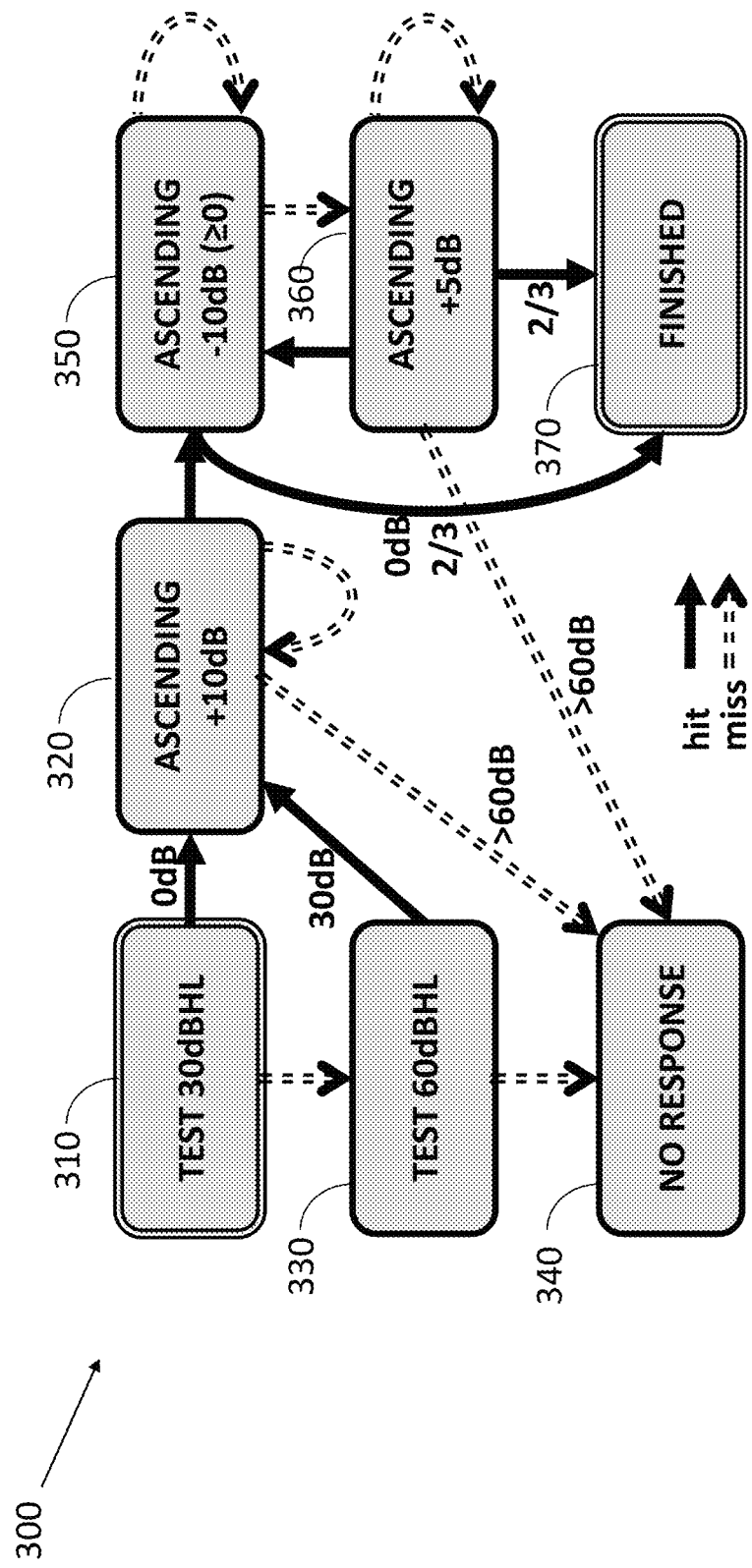
FIG. 3 is a flow diagram of a testing protocol for a given tone, according to the prior art.

FIG. 3 is a flow diagram showing a prior art example of a testing protocol 300 for a given tone, which may be operated by systems and methods, such as system 100 and/or method 200 in accordance with the prior art. For example, the testing protocol 300 may be performed per frequency (for each ear) by system 100. In some cases, a calibration process as illustrated in FIG. 2 is performed only once prior to the hearing test. In some instances, a calibration process is not performed (e.g. for measuring the calibration transfer) at all. It should be noted that in FIG. 3 all gain levels are in dBHL and gain jumps in dB. First, at step 310 a tone (TEST) at 30 is played. If a hit is identified (a positive indication from the subject), then at step 320 go to ASCENDING (+10) state with gain=0. Otherwise, if no indication received from the subject, at step 330 play a tone (TEST) at 60. If hit, go to step 320 to ASCENDING (+10) state with gain=30. Otherwise, mark "no response" at step 340 and go to next tone. In ASCENDING (+10) step 320, play a tone at current gain. If hit, go to DESCENDING state 350 with gain decreased by 10. If miss and gain is less than or equal to 60, go to ASCENDING (+10) 320 state with gain increased by 10. If miss and gain is over 60, mark "no response" (step 340) and go to next tone. In DESCENDING state 350, play tone at current gain. If hit and gain is positive, go to DESCENDING state with gain decreased by 10. If hit and under 0, go to DESCENDING state with the same gain. If miss go to ASCENDING (+5) state 360 with gain increased by 10. In ASCENDING (+5) state 360 play tone at current gain. If hit, go to DESCENDING state 350 with gain decreased by 10. If miss go to ASCENDING with gain increased by 5. If gain over 60, mark "no response" (step 340) and go to next tone. At any point keep a table of the hit/miss history per gain level. Upon hit, if two out of latest three tones were marked hit, go to FINISHED state 370 and mark gain.

According to some embodiments, a testing protocol is based on the Hughson-Westlake (Ascending-Descending/Up-Down) technique, which is a commonly used protocol for testing. Other protocols may also be used. Generally, for each tone, the tone output starts low and is raised (+10 dB jumps) until the patient responds. The tone output is then lowered (−10 dB) until the patient ceases to respond. The tone output is then raised (+5 dB) until the patient responds. Gain level is determined when the level is found at which the patient responds more often than not.

Figure 4:
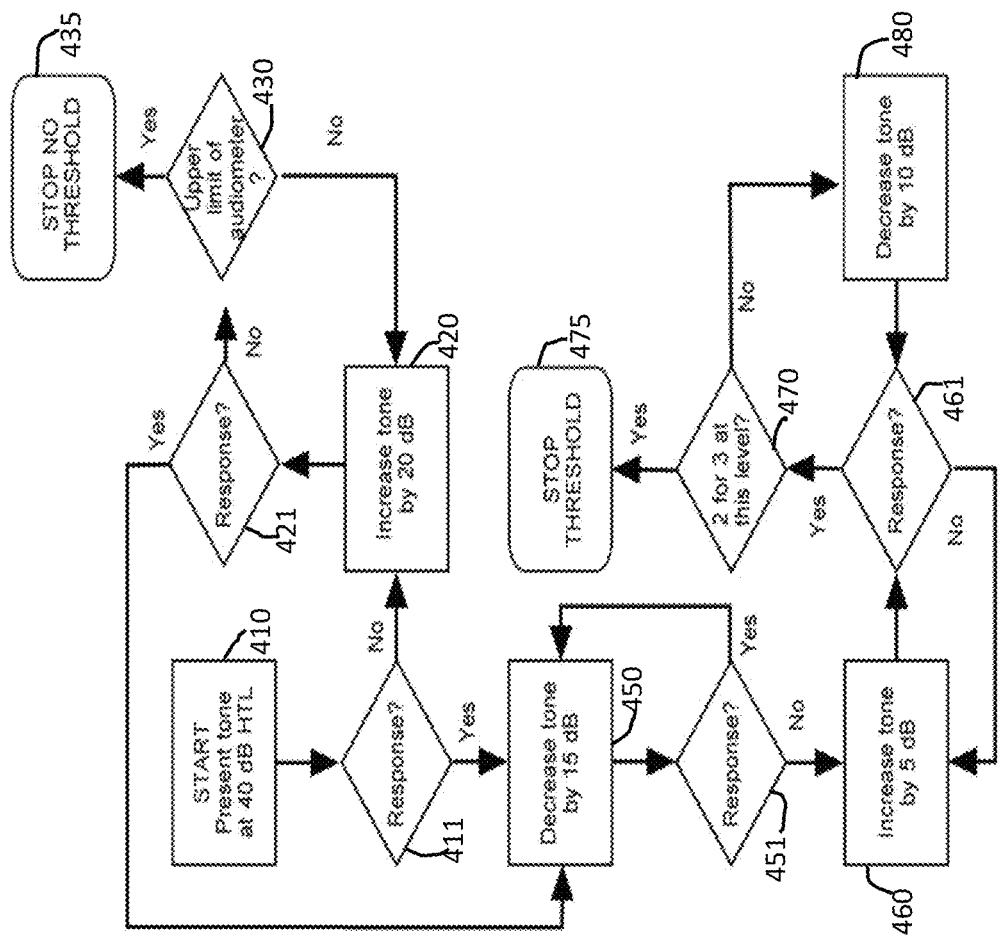
FIG. 4 is a hearing test designed to be conducted by a state machine, without human judgment being used, by a deterministic automaton, according to the prior art.

In some embodiments, the test is designed so it can be conducted by a state machine, without human judgment being used, for example by a deterministic automaton. As can be seen in FIG. 4, a modified test protocol flow, based on the Hughson-Westlake technique, (known in the art, and adapted from Martia 1983) is shown.

As can be seen with reference to FIG. 4, the test starts with an initial tone at 40 db HL (step 410). If there is no response (step 411) the tone is increased by 20 db (step 420). If there is no response (step 421), and this is the upper limit of the audiometer (step 430), then stop the test, there is no threshold to be set (step 435). If there is a response (step 411 or 421), then decrease the tone by 15 db (step 450). Keep decreasing the tone by 15 db until there is no response (step 451), then increase the tone by 5 db 460. Keep increasing the tone by 5 db until there is a response (step 461). If two of the latest three tones were detected at this level (step 470), stop the test, and establish current gain as threshold (step 475). Otherwise, decrease the tone by 10 dB (step 480), and check response (step 461).

Figure 5:
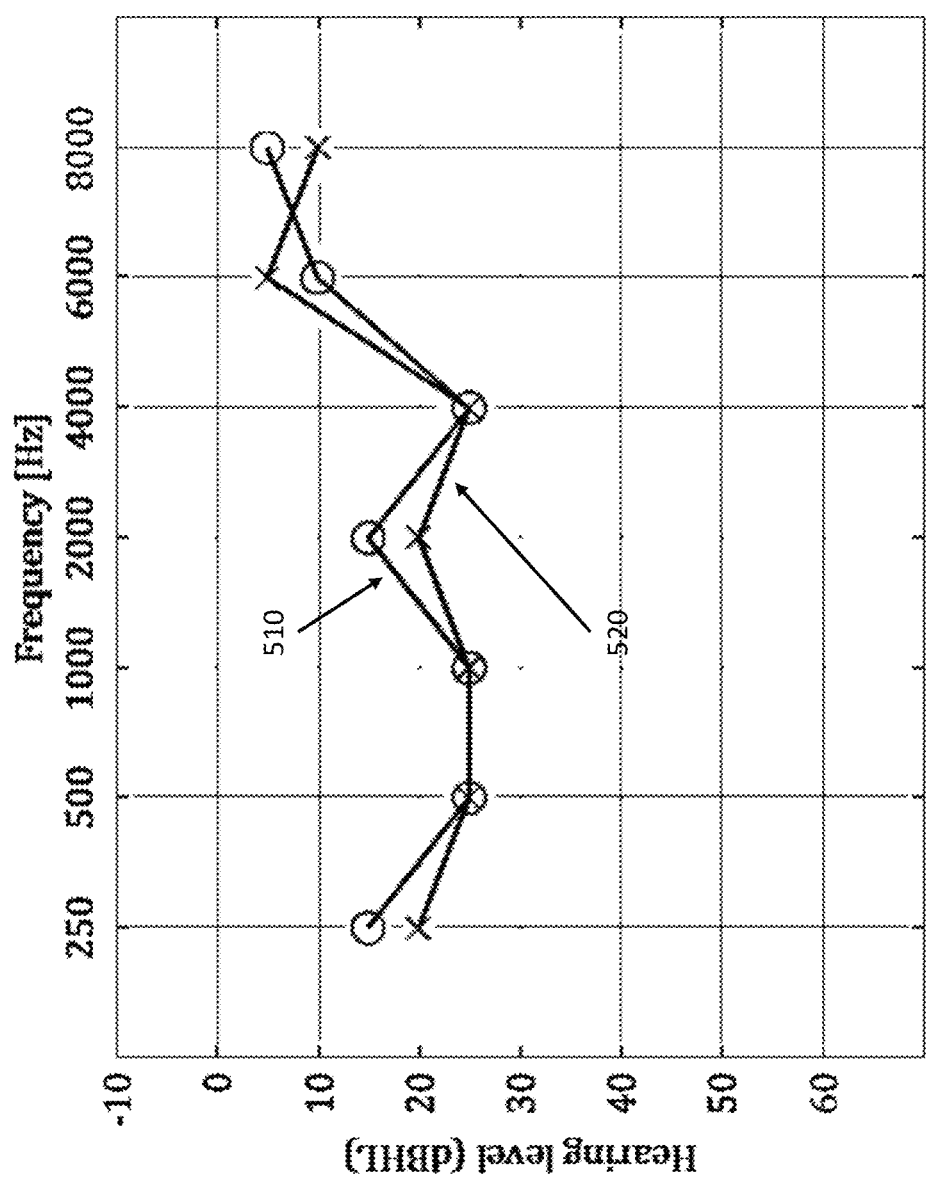
FIG. 5 is a graphic illustration of an audiogram method, where the audiogram is the frequency response of a human ear, in accordance with embodiments of the present invention.

According to some embodiments, an Audiogram Aggregation method is provided, as depicted in FIG. 5. An audiogram is a conventional description of human hearing. It consists of two charts, or curves, one for each ear, each measured in decibels per frequency, and compared to the hearing of an average young person, which is referred to as 0 dBHL (zero decibel hearing level) in all frequencies. The O's stand for the right ear 510 and X's for the left ear 520. These are standards familiar to all audiologists. The zero level in FIG. 5 is the standard for a young healthy individual as described by ANSI (1996).

The audiogram values indicate how much to amplify at each frequency to get the desired 0 dBHL. Higher values mean greater hearing loss, and more power needed.

An audiometric self-test can be taken many times. By the law of large numbers, it may be assumed that by repeating the test enough times the average will become an increasingly better evaluation of the hearing level (or alternatively, that the error vanishes), therefore precision can be better than that of normal tests taken at very few occasions. This would be true if all samples were taken from the same underlying distribution. However, these assumptions may be challenged by: Human error—which can be attributed to numerous causes; Different environmental noise—depending on location, time of day and specific noise factors (AC, cars, wind, rain, etc.); and fluctuations in hearing level—changes in airflow conduction in the ear, level of awareness, adrenalin, etc.

Figure 6:
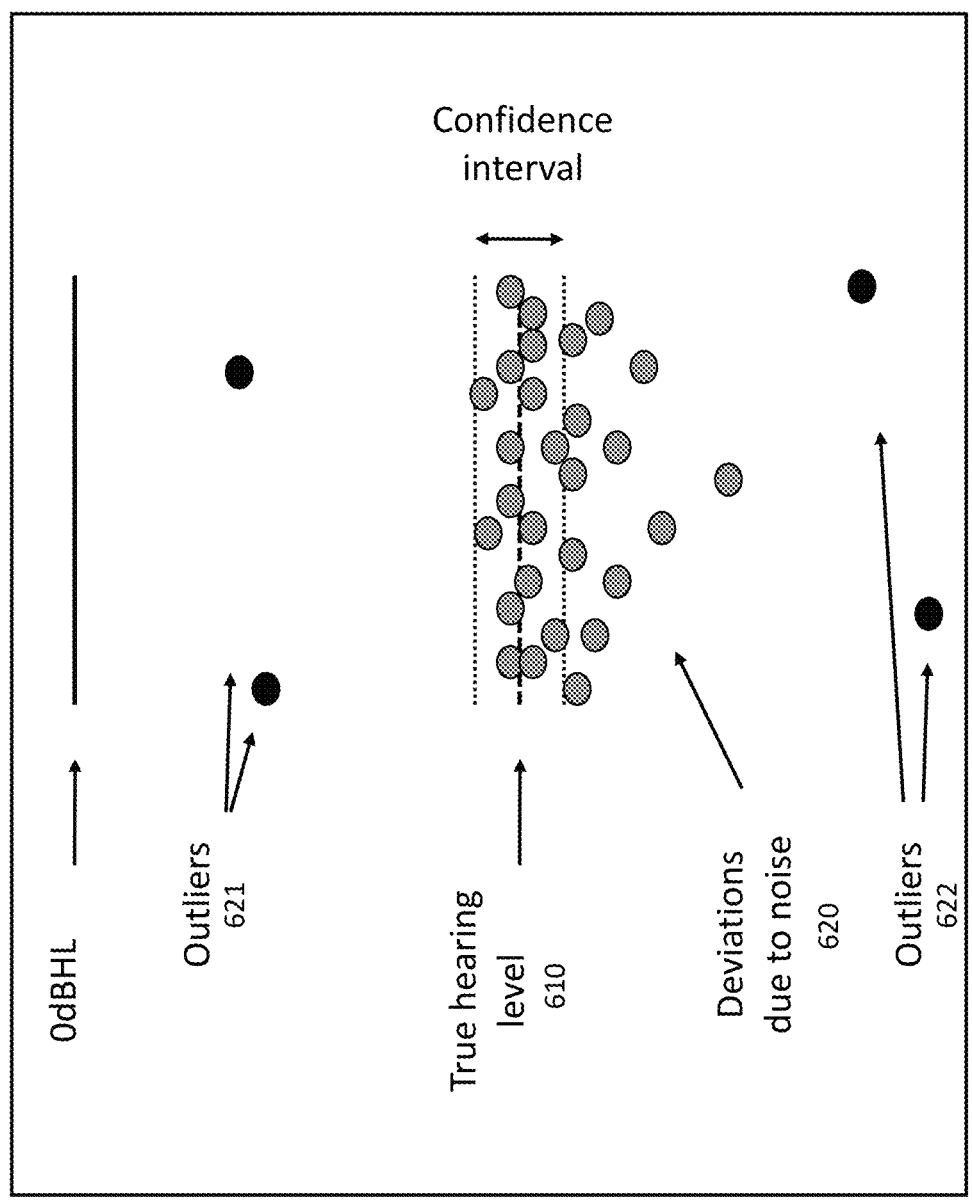
FIG. 6 is an illustration of the Audiogram Aggregation model based on the assumption that the user has one true hearing level per frequency, or audiogram A(f), obstructed by noise factors, in accordance with embodiments of the present invention.

In accordance with some embodiments, depicted in FIG. 6, a useful approximation is generated based on the following guidelines: The user has one true hearing level per frequency, or audiogram $A(f)$ 610; Deviations, $\Delta A$ 620, are a function of the properties of the noise, $N(t)$ at the time of recording: $X(f)=A(f)+\Delta A(f, N(t))$; and deviations that are not a function of the noise (human error, plugged ears, and so on) create outliers 621 and 622. Since readings can be as low as the true hearing level, therefore no noise can help us hear better. Therefore, the true or substantially accurate level—the infimum (greatest lower bound) of the measurements, which are not outlier noises, may be evaluated from the readings, and from noise recordings.

According to some embodiments, once a digital audiogram is acquired for a user's device, the user audiogram is applied, for example to a physical layer of a selected device. The selected device may be for example, a smartphone, tablet, computer, television, console, smart speaker etc., including one or more processing units configured to integrate the audiogram's digital code into the audio output processing, thereby outputting audio in accordance with the user's audiogram.

According to further embodiments, once a digital audiogram is acquired for a user's device, the user audiogram is applied to a content layer or application layer that is executed by the selected device, for example, YouTube, iTunes, Netflix, audiobooks, radio stations, conferencing software, etc., to enable the application to integrate the audiogram's digital code into the audio output, thereby outputting audio in accordance with the user's audiogram.

According to some embodiments, once a digital audiogram is acquired for a device user, the user audiogram is applied to a communications layer of communications provider, for example, an ISP, communications provider, infrastructure provider etc., to enable the communications system to integrate filters corresponding to the audiograms into the audio output processing, thereby outputting audio in accordance with the user's audiogram.

Figure 7:
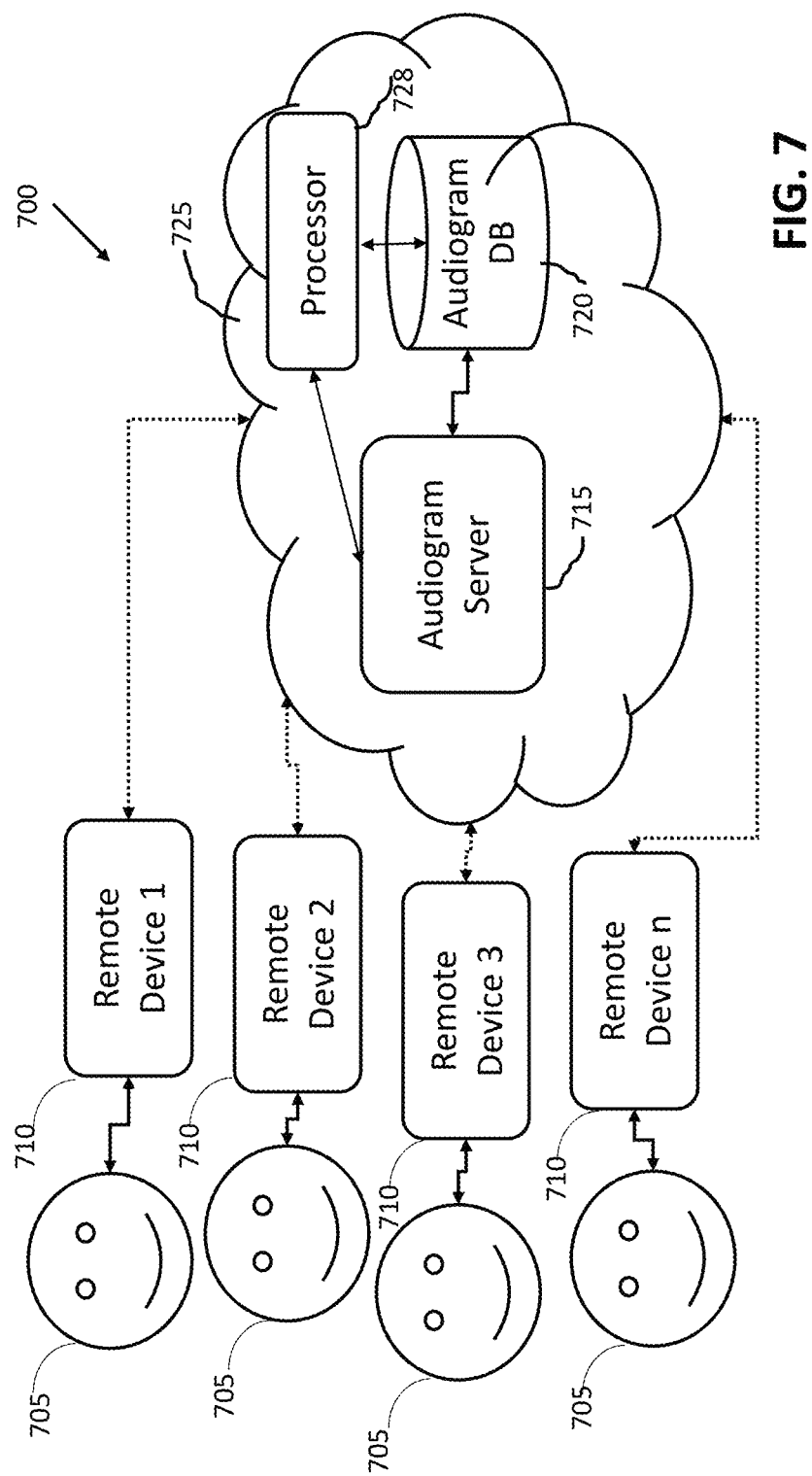
FIG. 7 is a schematic system diagram depicting a plurality of applications based on a digital audiogram connected to the cloud, in accordance with embodiments of the present invention.

FIG. 7 is a schematic diagram depicting a server-based audiogram analysis engine system 700 for providing an audio for each of a plurality of devices and applications based on an audiogram such as a digital audiogram transmitted via the network to an audiogram server, according to embodiments. In some cases, the server-based audiogram analysis engine system 700 includes multiple users 705, using multiple remote communicating and/or computing devices or systems 710 (such as the device 105 or system 100 of FIG. 1), which may be in communication with an audiogram server 715, communicatively connected to an audiogram database 720 and/or a server processor 728, generally located or connected to a communications cloud 725. In operation, audiogram server 715 runs code, for example executed at server processor 728 or at the user's device processor, to enable remote testing of users, optionally using a variety of end user devices. Audiogram server 715 runs further code to analyze user audiogram related data and determine and design the best audio filter for the user. Audiogram server 715 delivers the filter specifications, or embedded code implementing the filter, to multiple applications and/or remote communicating and/or computing devices/systems 710 that handle digital audio before it is delivered to the user. Audiogram database 720 stores data from multiple users and/or user devices, including user audiogram data, and hardware configurations of user remote communicating and/or computing devices 710. Further, audiogram database 720 stores data audiogram data from different tests taken at different times and locations, for the purpose of precise evaluation of hearing, and specifically, under the influence of different noise profiles. Audiogram database 720 can also provide the service of a surveillance table, indicating deterioration in hearing before it has manifested to the extent that it is perceived by the user.

Figure 8:
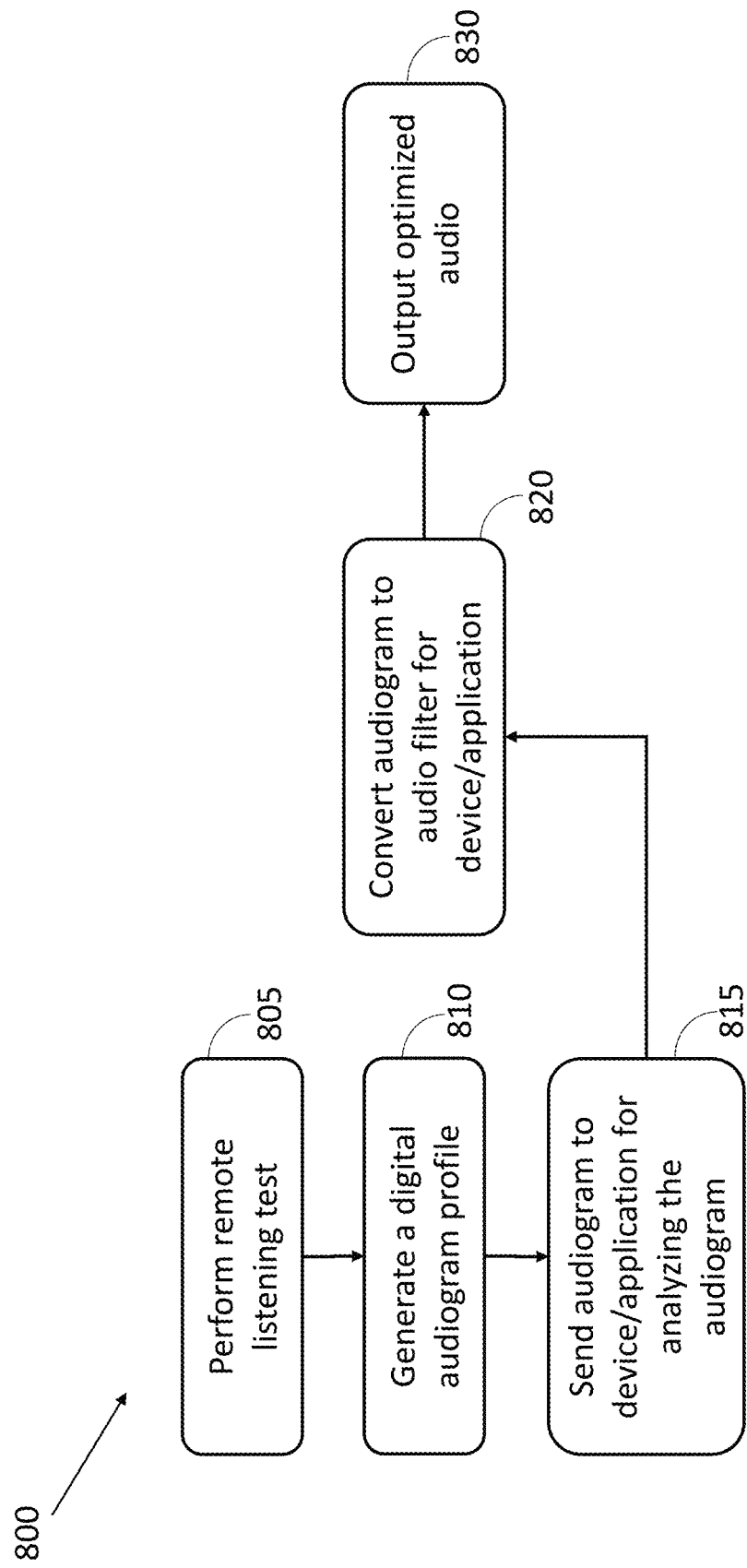
FIG. 8 is a flow diagram for execution of a digital audiogram in an audio playback system, in accordance with some embodiments of the present invention.

FIG. 8 is a flow diagram 800 of a method for executing a digital audiogram in an audio playback system, constructed according to embodiments. At step 805, a user performs a remote listening test, to generate at step 810 one or more audiograms such as cloud-based audiograms. In some cases, the remote test may be performed according to method 200 as illustrated in FIG. 2. At step 815 the acquired audiograms are sent to a device and/or application and/or cloud-based audiogram database, for example via a network server for analyzing the audiograms, and/or validate them, and/or update a user hearing or audiogram profile, and/or generate alerts if necessary regarding the user's hearing condition. A user hearing or audiogram profile may include a user's hearing condition and may be stored for example at audiogram database DB 720 or at the user's device database. At step 820 the analyzed audiograms are converted into an audio filter specification. In particular, this filter can be a linear infinite/finite impulse response (IIR/FIR) filter specified by a set of coefficients (as disclosed, for example, by Szopos et al. 2012). In some cases, other types of filters, linear and non-linear can be used for this purpose. The filter is configured to filter and/or adjust the audio output of the user's selected device audio player for generating an audio output according to the user's audiograms. At step 830 the audio filter calculated in step 820 is applied to an audio output from the selected device(s) or application(s).

In some embodiments, additional filters can be applied to the audio output as well, which are not specific to the user, for example, noise reduction for enhanced speech understanding by, for example, a 300-4000 Hz bandpass filter, or dynamic-range power maximization (Arfin et al. 2009).

In some embodiments, the user's audiogram is integrated into a user audio profile or signature. The user's profile may also include some of the following data: the time and place where tests were conducted, their results, and characteristics of the environmental noise that was present when taken; the time, place, duration, application, and hardware with which a filter was applied; personal information such as age, sex, occupation, and place of residence; and pertinent medical information such as other hearing tests conducted by the user, and information regarding the user's hearing aids.

In some embodiments, the user's audiogram is generated in an audiogram digital format that may be executed by multiple vendors in external devices, programs, applications, etc.

In some embodiments, the user's audiogram may include personal preferences, for example, listening preferences for different types of audio etc.

According to certain embodiments, a user audio output device can be used to improve phone calls and other mobile audio output to a user, from a phone device, audio device, earphones etc. For example, if a user A using a device in accordance with embodiments is carrying out a conversation with another user B, and even if user B is not using a supported device capable of audio filtering, in accordance with embodiments, the audio output from the device of user A is improved for user B's hearing, according to user B's audiogram, as recorded in the Audiogram Database 720.

According to certain embodiments, a user audio output device can share audiometric data with other devices (TV, PC, car stereo, etc.) if the device supports a standard interface for audio equalization. In some cases, the audiometric data may include the user's audiogram, a filter specification, or preferences related to the user's hearing.

According to some embodiments, the user's audiogram is integrated into a processor of noise cancellation earphones/headphones, thereby enabling the earphones to be used as audio enhancing devices and/or as hearing aid devices. For example, received audio sounds may be filtered and optionally re-generated with filtered audio signals, amplified signals etc., to enable transmitting of personalized audio output.

Further, since the user's audiogram is cloud based, it may be integrated into multiple connected devices and systems, to allow seamless application of personalized audio across different devices, anywhere.

In accordance with some embodiments, there are provided methods and systems for transforming Noise-Canceling Headphones to Noise-Canceling Hearing Aids, as described with reference to FIGS. 9A-9C.

Those of skill in the art will also recognize that suitable noise canceling headphones 905 may be, by way of non-limiting examples, a SONY® WH-1000XM2, or Philips® Fidelio NC1, Bose® QuietComfort 35, or the like.

According to some embodiments, the noise-canceling headphones are the noise-canceling headphones described in U.S. Pat. No. 8,045,726, incorporated herein by reference. For example the noise-canceling headphones may include a cancel signal generator that receives ambient noise via an electro-acoustic transducer and generates and outputs a cancel signal, eliminating the noise; and a speaker unit that outputs an audio signal and a cancel signal, and connects the cancel signal generator to a first terminal of two input terminals of the speaker unit and connects a sound source of an audio signal to a second terminal thereof, whereby obtaining the noise-canceling headphones with which one can enjoy music with high quality without a change in the sound quality and volume between when a noise-canceling function is activated and when deactivated.

In some cases, the noise-canceling headphones 905 is connectable to a portable computing platform having a processor and one or more microphones 906 and/or speakers 908.

A noise canceling hearing aid may be defined, in some embodiments, as a device configured to adjust, rather than amplify, environmental sound to the user. It is different from a conventional hearing aid because it attenuates (or cancels) the original environmental audio actively, rather than passively blocking it (as a hearing aid typically does), and additionally emits the same audio, with necessary adjustments specific to the user. Equivalently, it can be stated that, due to the well-known superposition principle, a noise canceling hearing aid emits the difference between the original ambient signal and the adjusted signal, added in-phase to the original ambient signal.

Figure 9A:
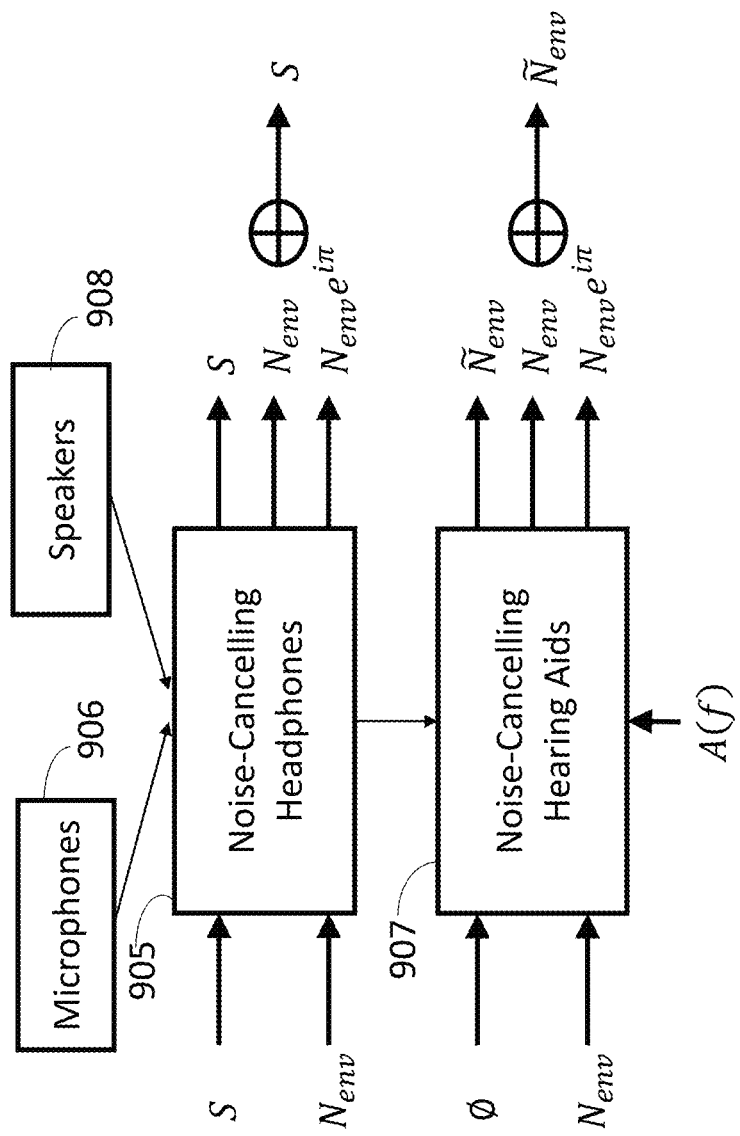
FIGS. 9A-9C are a series of work flow diagrams showing examples of improving audio output with noise cancellation headphones, according to the principles of the present invention.
Figure 9B:
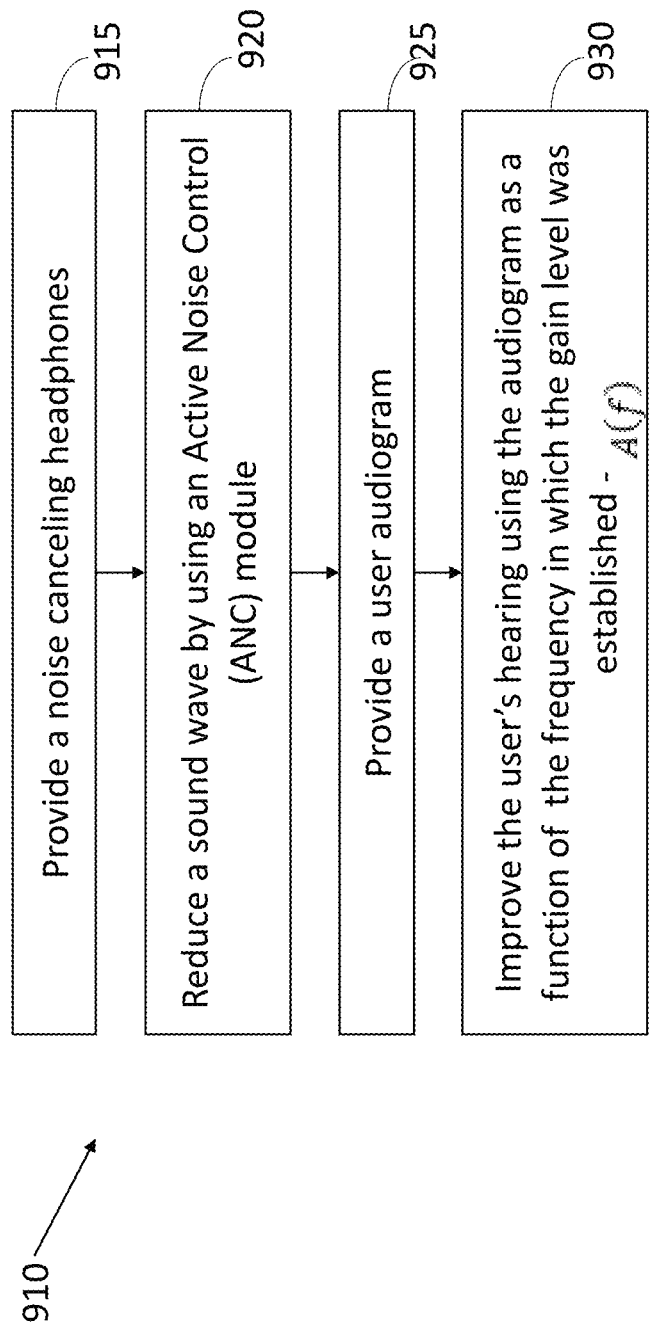

FIG. 9A illustrates noise canceling headphones 905 transformed to a noise canceling hearing aid 907, according to a transformation method 910 illustrated in FIG. 9B.

At step 915 the noise canceling headphones 905 are provided. At step 920, an Active Noise Control (ANC) module is used for reducing a sound wave, for example by superimposing an additional source with equal amplitude and inverted phase at all times. For example, the noise-canceling headphones 905 may employ the ANC method to reduce a sound originating from the environment and perceived by the user wearing them. The method includes for example, superimposing a desired signal S on a signal emitted by the speakers. The desired effect is to replace the environmental noise $N_{env}$ with a signal S chosen by the user, e.g. music from an audio player. To achieve this, in some embodiments, the noise-canceling headphones 905 may be connected to one or more microphones 906 and speakers 908 for example at each ear, and real-time processing, necessary for ANC, is used to relay the sound picked-up by each microphone and mix it (in antiphase) with the signal.

At step 925 a user audiogram, such as a digital audiogram, is provided to the noise canceling headphones, for example as illustrated in FIG. 8. At step 930, the user's audiogram is used with the noise-canceling headphones 905 to improve the user's hearing by applying the gain levels recorded in the user's audiogram for each frequency, in the following manner: the audiogram, which functions as a characterization of a person's threshold hearing gain level in units of dBHL, is marked A(f), where f is the frequency in which the gain level was established. Further, a signal S is denoted as the signal S filtered by a filter applying a gain at each frequency equivalent to A(f), for example using a finite impulse response (FIR) filter. Additionally, by dropping the input signal S, and replacing the output with the filtered environmental noise, the method effectively replaces sound input from the environment with appropriately filtered sound.

Figure 9C:
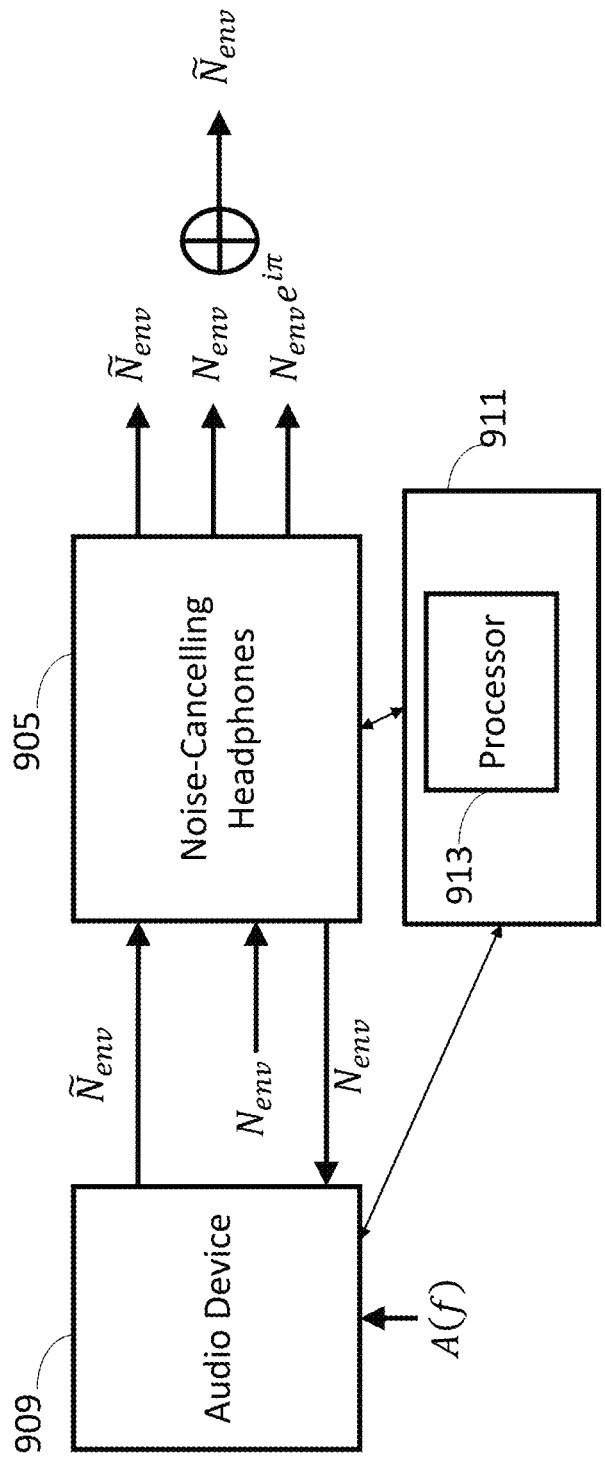

In some embodiments, as illustrated in FIG. 9C, the above described process is applied to multiple hardware devices or systems, without requiring any change to the hardware configuration of these devices or systems. For example, the noise canceling headphones may be connectable to an audio device 909 and to a portable computing platform 911, such as a mobile phone having a processor 913. In such cases, an appropriate software driver, executed for example by the processor 913, may include instructions for providing a signal input S, to enable the audio device 909 to acquire the noise detected by the headphones microphones $N_{env}$. The audio device 909 can then filter this signal and deliver $\tilde{N}_{env}$ as the input signal to the headphones. The result in some cases is equivalent to the proposed noise-canceling hearing aid system, but no additional hardware is required.

According to some embodiments, a user audiogram is applied to a vehicle audio output device or system, to provide enhanced audio output for a driver or user of the vehicle or transporter.

According to some embodiments, a user audiogram is applied to a call center or other typically noisy environment, to improve audio output to users in the noisy environment.

According to some embodiments, a user audiogram is applied to mobile communication devices, such as phones, smart phones, tablets, wearable devices etc., to enhance phone call and other audio output quality.

According to some embodiments, a user audiogram is applied to mobile communication devices, such as phones, smart phones, tablets, wearable devices etc., to enhance music or other audio output quality.

According to some embodiments, a user audiogram is applied to multiple music or other audio related applications running on a computer or communications devices, such as music playing programs, audiobook players, Podcasts players, games etc.

According to some embodiments, a user audiogram is applied to televisions, computer screens, consoles, and other entertainment systems or devices, optionally applying improved audio to directional speakers.

According to some embodiments, a user audiogram is applied to computers, PCs, mobile devices, televisions and other screening devices running audio-based content programs or applications, to enable improved audio output for content applications such as YouTube, Netflix, cable TV, Spotify, Apple music, online radio stations, games etc.

According to some embodiments, a user audiogram is applied to a cloud-based Conference Call program, to improve output to conference call users.

According to some embodiments, a user audiogram is applied to a smart home or other smart environments that integrate audio output. In some examples, a user audiogram can be applied to digital assistants such as Alexa, Sin, and other personal robots, guides, assistants, to improve communication and/or content output for user(s).

According to some embodiments, a user audiogram is applied to broadcast radio, typically on radio player hardware.

According to some embodiments, a user audiogram is applied to an audio output channel, device, application etc., to provide audio output adapted to a user's accent and/or dialect.

In some embodiments, no audio output device calibration is required.

The systems and methods of the embodiments can be implemented, at least in part, as a machine configured to receive a computer-readable medium storing computer-readable instructions. The instructions can be executed by computer-executable components integrated with the application, applet, host, server, network, website, communication service, communication interface, hardware/firmware/software elements of a user computer or mobile device, or any suitable combination thereof. Other systems and methods of the embodiments can be embodied and/or implemented at least in part as a machine configured to receive a computer-readable medium storing computer-readable instructions. The instructions can be executed by computer-executable components integrated by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor or any suitable dedicated hardware device that can (alternatively or additionally) execute the instructions.

The present invention provides computer control systems that are programmed to implement the methods thereof. FIG. 10 shows a computer system 1001 suitable for incorporation with the methods and apparatus in accordance with some embodiments of the present invention. The computer system 1001 can process various aspects of information, such as, questions and answers, responses and statistical analyses. The computer system 1001 can be an electronic device of a user or a computer system that is remotely located with respect to the electronic device. The electronic device can be a mobile electronic device.

The computer system 1001 includes a central processing unit 1005 (CPU, also "processor" and "computer processor" herein), which can be a single core or multi core processor, or a plurality of processors for parallel processing. The computer system 1001 also includes a memory location or memory 1010 (e.g., random-access memory, read-only memory, flash memory), an electronic storage unit 1015 (e.g., hard disk), a communication interface 1020 (e.g., network adapter) for communicating with one or more other systems, and peripheral devices 1025, such as cache, other memory, data storage and/or electronic display adapters. The memory 1010, storage unit 1015, interface 1020 and peripheral devices 1025 are in communication with the CPU 1005 through a communication bus (solid lines), such as a motherboard. The storage unit 1015 can be a data storage unit (or data repository) for storing data. The computer system 1001 can be operatively coupled to a computer network ("network") 1030 with the aid of the communication interface 1020. The network 1030 can be the Internet, an internet and/or extranet, or an intranet and/or extranet that is in communication with the Internet. The network 1030 in some cases is a telecommunication and/or data network. The network 1030 can include one or more computer servers, which can enable distributed computing, such as cloud computing. The network 1030, in some cases with the aid of the computer system 1001, can implement a peer-to-peer network, which may enable devices coupled to the computer system 1001 to behave as a client or a server.

The CPU 1005 can execute a sequence of machine-readable instructions, which can be embodied in a program or software. The instructions may be stored in a memory location, such as the memory 1010. The instructions can be directed to the CPU 1005, which can subsequently program or otherwise configure the CPU 1005 to implement methods of the present disclosure. Examples of operations performed by the CPU 1005 can include fetch, decode, execute, and writeback.

The CPU 1005 can be part of a circuit, such as an integrated circuit. One or more other components of the system 1001 can be included in the circuit. In some cases, the circuit is an application specific integrated circuit (ASIC).

The storage unit 1015 can store files, such as drivers, libraries and saved programs. The storage unit 1015 can store user data, e.g., user preferences and user programs. The computer system 1001 in some cases can include one or more additional data storage units that are external to the computer system 1001, such as located on a remote server that is in communication with the computer system 1001 through an intranet or the Internet.

The computer system 1001 can communicate with one or more remote computer systems through the network 1030. For instance, the computer system 1001 can communicate with a remote computer system of a user (e.g., a parent). Examples of remote computer systems and mobile communication devices include personal computers (e.g., portable PC), slate or tablet PC's (e.g., Apple® iPad, Samsung® Galaxy Tab), telephones, Smart phones (e.g., Apple® iPhone, Android-enabled device, Blackberry®), personal digital assistants, wearable medical devices (e.g., Fitbits), or medical device monitors (e.g., seizure monitors). The user can access the computer system 1001 with the network 1030.

Methods as described herein can be implemented by way of machine (e.g., computer processor) executable code stored on an electronic storage location of the computer system 1001, such as, for example, on the memory 1010 or electronic storage unit 1015. The machine executable or machine-readable code can be provided in the form of software. During use, the code can be executed by the CPU 1005. In some cases, the code can be retrieved from the storage unit 1015 and stored on the memory 1010 for ready access by the CPU 1005. In some situations, the electronic storage unit 1015 can be precluded, and machine-executable instructions are stored on memory 1010.

The code can be pre-compiled and configured for use with a machine have a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 401, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that include a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1001 can include or be in communication with an electronic display 1035 that includes a user interface (UI) 1040 for providing, for example, questions and answers, analysis results, recommendations. Examples of UI's include, without limitation, a graphical user interface (GUI) and web-based user interface.

Methods and systems of the present disclosure can be implemented by way of one or more algorithms and with instructions provided with one or more processors as disclosed herein. An algorithm can be implemented by way of software upon execution by the CPU 1005. The algorithm can be, for example, random forest, graphical models, support vector machine or other.

The above steps show a method of a system in accordance with some embodiments of the invention, and a person of ordinary skill in the art will recognize many possible variations based on the teaching described herein. The steps may be completed in a different order. Steps may be added or deleted. Some of the steps may include sub-steps. Many of the steps may be repeated as often as if beneficial to the platform.

Each of the examples as described herein can be combined with one or more other examples. Further, one or more components of one or more examples can be combined with other examples.

Although the detailed description contains many specifics, these should not be construed as limiting the scope of the invention but merely as illustrating different examples and aspects thereof. It should be appreciated that the scope of the disclosure includes other embodiments not discussed in detail above. Various other modifications, changes and variations which will be apparent to those skilled in the art may be made in the arrangement, operation and details of the method and apparatus of the present disclosure provided herein without departing from the scope of the invention as described herein.

While preferred embodiments of the present disclosure have been shown and described herein, it will be obvious to those skilled in the art that such embodiments are provided by way of example only. Numerous variations, changes, and substitutions will be apparent to those skilled in the art without departing from the scope of the present invention. It should be understood that various alternatives to the embodiments described herein may be employed without departing from the scope of the present invention. Therefore, the scope of the present invention shall be defined solely by the appended claims and the equivalents thereof.

The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the scope of the invention.

The invention claimed is:

1. A system for providing audio output, the system comprising:
   a remote computing device including a processor and an audio unit configured to generate one or more output signals of arbitrary amplitude;
   earphones connectable to the computing device, configured to output said output signals; and
   a microphone configured to record the power level of said output signals and calculate a proportionality constant for each frequency of said output signals; wherein said processor is further configured to:
      analyze the proportionality constant for each frequency of one or more feedback signals from said one or more earphones to yield calibration data;
      adjust the amplitude or frequency based at least on the calibration data to calibrate the device;
      generate one or more audiograms resulting from a hearing test using the calibrated device; and
      adjust a device power level according to said one or more audiograms.

2. The system of claim 1, wherein said processes is configured to calculate a fractional amplitude coefficient for each of said feedback signals for providing said calibration data.

3. The system of claim 1, wherein said hearing test is executed by said processor according to a state deterministic automaton.

4. The system of claim 1, wherein said audiograms are applied to one or more selected remote devices having a processor, said processor being configured to adjust audio power of said selected device, based on said audiograms.

5. The system of claim 1, wherein said device is a mobile communication device comprising wireless communication circuitry to communicate with a remote server, and wherein the processor comprises transmission instructions to transmit the audiogram to the remote server.

6. The system of claim 5, wherein in response to said transmission instructions the audiograms are further integrated in said remote server database for adjusting an audio output control of one or more contents or application in said remote server database in accordance with the integrated audiogram.

7. The system of claim 6, configured so that said audiograms can be applied to a communication layer of said remote server for adjusting an audio output control of said communication layer in said remote server database in accordance with the integrated audiogram.

8. The system of claim 7, wherein said content or application is selected from the group consisting of: YouTube; iTunes; Netflix; audiobooks; radio stations; and conferencing software.

9. The system of claim 1, wherein said one or more earphones are selected from the group consisting of: noise cancellation earphones; wireless earphones; and wired earphones.

10. The system of claim 1, configured so that said audiograms are generated in a digital format.

11. The system of claim 1; wherein said audiograms comprise personal preferences of said user.

12. The system of claim 1, configured so that said audiograms are sharable with other devices or applications.

13. The system of claim 1, configured so that said audiograms can be applied to digital assistant devices.

14. The system of claim 1, configured so that said audiograms can be applied an audio output channel to provide audio output adapted to a user's accent or dialect.

15. The system of claim 1, configured so that said audiograms can be integrated into a processor of noise cancellation earphones for converting said noise cancellation earphones to audio enhancing devices or hearing aid devices.

16. The system of claim 15, wherein said processor is adapted to filter said audio signals received at said noise cancellation earphones and to amplify said audio signals to yield a personalized audio output by said noise cancellation earphones.

17. A server-based audiogram analysis engine system, the system comprising:
   a remote server, said remote server being in communication with a database and a remote processor;
   a plurality of remote devices connectable respectively to a plurality of earphones, wherein each of said plurality of remote devices comprises:
      a computing platform having a processor;
      an audio unit configured to generate respectively one or more output signals of arbitrary amplitude to said plurality of headphones; and
      communication circuitry to communicate with said remote server; wherein each of said remote devices is configured to:
         perform a hearing test to one or more users, the hearing test comprising: generating one or more output signals of arbitrary amplitude to yield an audiogram profile respectively for each of said users; and
         transmit said audiogram profile to said remote server, wherein said remote server comprises instructions to:
         analyze said audiogram profiles; and
         convert said audiogram profiles to yield a personalized audio filter for each of said plurality of remote devices.

* * * * *